United States Patent
Keller et al.

(10) Patent No.: US 8,334,971 B2
(45) Date of Patent: Dec. 18, 2012

(54) APPARATUS FOR IMAGING THE INNER SURFACE OF A CAVITY WITHIN A WORKPIECE

(75) Inventors: Hubert Keller, Constance (DE); Michael Rudolf, Constance (DE)

(73) Assignee: Hommel-Etamic GmbH, Villingen-Schwenningen (DE)

( * ) Notice: Subject to any disclaimer, the term of this patent is extended or adjusted under 35 U.S.C. 154(b) by 189 days.

(21) Appl. No.: 12/662,813

(22) Filed: May 4, 2010

(65) Prior Publication Data

US 2011/0001984 A1 Jan. 6, 2011

(30) Foreign Application Priority Data

May 4, 2009 (DE) .......................... 10 2009 019 459

(51) Int. Cl.
*G01N 21/00* (2006.01)
(52) U.S. Cl. ................................. 356/237.2; 356/241.1
(58) Field of Classification Search .... 356/241.1–241.6, 356/237.1–237.5
See application file for complete search history.

(56) References Cited

U.S. PATENT DOCUMENTS

| | | | |
|---|---|---|---|
| 3,552,820 A | 1/1971 | Brachvogel | |
| 4,394,683 A | 7/1983 | Liptay-Wagner et al. | |
| 4,566,763 A | 1/1986 | Greguss | |
| 5,058,178 A * | 10/1991 | Ray | 382/150 |
| 5,473,474 A | 12/1995 | Powell | |
| 6,462,815 B1 * | 10/2002 | Drabarek et al. | 356/241.1 |
| 6,621,516 B1 * | 9/2003 | Wasson et al. | 348/84 |
| 7,164,476 B2 * | 1/2007 | Shima et al. | 356/241.1 |

FOREIGN PATENT DOCUMENTS

| | | |
|---|---|---|
| CH | 660 629 A5 | 5/1987 |
| DE | 31 23 703 C2 | 3/1982 |
| DE | 32 32 904 C2 | 3/1984 |
| DE | 3232904 A1 * | 3/1984 |

(Continued)

OTHER PUBLICATIONS

Kammel, Sören "Deflektometrische Untersuchung spiegelnd reflektierender Freiformflächen" [Deflectometric analysis of specularly reflective free-form surfaces], Institut für Meβ—und Regelungstechnik Karlsruhe (TH), Schriftenreihe Nr. 004 [Institute for Measurement and Control Engineering, University of Karlsruhe (TH), Publication Series No. 004], http://www.uvka.de/univerlag/volltexte/2005/50/, ISSN 1613-4214, ISBN 3-937300-28-7, published 2005 (127 pages).

(Continued)

*Primary Examiner* — Hoa Pham
(74) *Attorney, Agent, or Firm* — Shlesinger, Arkwright & Garvey LLP (57) ABSTRACT

An apparatus for imaging the inner surface of a cavity in a workpiece has an optical system including a panoramic field of view that is linked to an imager and a downstream evaluation device by an image communication link. The apparatus furthermore has an illumination system including a light source to illuminate an imaging region of the inner surface, which region has been captured by the optical system. According to the invention, the illumination system is disposed in such a way relative to optical system, and for which the beam path is selected in such a way, that a first axial section of the imaging region is able to be illuminated under brightfield illumination, while simultaneously a second axial region spaced apart from the first axial region is able to be illuminated under darkfield illumination.

17 Claims, 11 Drawing Sheets

FOREIGN PATENT DOCUMENTS

| | | |
|---|---|---|
| DE | 43 20 845 C1 | 10/1994 |
| DE | 44 16 493 A1 | 11/1995 |
| DE | 202 14 856 U1 | 2/2003 |
| DE | 10 2007 031 358 A | 3/2009 |
| EP | 1 321 793 B1 | 6/2003 |
| GB | 2126715 A * | 3/1984 |
| WO | WO 2009/003692 A1 * | 1/2009 |

OTHER PUBLICATIONS

U.S. Appl. No. 12/805,053, filed Jul. 2010, Wegmann.

U.S. Appl. No. 12/923,412, filed Sep. 2010, Arnold.

U.S. Appl. No. 13/041,196, filed Mar. 2011, Keller et al.

U.S. Appl. No. 13/096,375, filed Apr. 2011, Seewig.

U.S. Appl. No. 13/214,764, filed Aug. 2011, Volk.

U.S. Appl. No. 13/073,625, filed Mar. 2011, Arnold.

"Spiegellinsenobjektiv aus Wikipedia, der freien Enzyklopadie" (5 pp.) downloaded Apr. 28, 2009; and Machine translation thereof(5 pp.)(10 pp. total).

* cited by examiner

APPARATUS FOR IMAGING THE INNER SURFACE OF A CAVITY WITHIN A WORKPIECE

CROSS-REFERENCE TO RELATED APPLICATIONS

This application claims the priority of German application no. 10 2009 019 459.2-52, filed May 4, 2009, and which is incorporated herein by reference.

FIELD OF THE INVENTION

The invention relates to an apparatus of the type for imaging the inner surface of a cavity in a workpiece.

BACKGROUND OF THE INVENTION

An apparatus of the relevant type for the imaging of the inner surface of a cavity in a workpiece is known from WO 2009/003692, the apparatus including an optical system comprising a panoramic field of view that is linked to an imager and downstream evaluation device by an image communication link. The known device furthermore includes an illumination system to illuminate an imaging region of the inner surface, which region is captured by the optical system.

Systems of this type are employed, for example, during the inspection of cylinder bores in crankcases, and function to image the radial inner surface of the cylinder bore and then to examine whether the bore meets specified requirements in terms of surface quality.

OBJECTS AND SUMMARY OF THE INVENTION

An object of the invention is to overcome the drawbacks of the prior art.

An object of the invention is to provide an apparatus for imaging the inner surface of a cavity in a workpiece, the capabilities of which, in terms of imaging the inner surface, have been expanded.

This object is achieved by the invention as set forth below, the invention including an apparatus for imaging the inner surface of a cavity in a workpiece, which apparatus includes an optical system having a panoramic field of view that is linked to an imager and a downstream evaluation device with an image communication link; and there is an illumination system having a light source to illuminate an imaging region of the inner surface captured by the optical system. The illumination system is disposed in such a way relative to the optical system, and for which a beam path of the light source is selected in such a way, that a first axial section of the imaging region is able to be illuminated under brightfield or bright field illumination, while simultaneously a second axial region spaced apart from the first axial region is able to be illuminated under darkfield or dark field illumination.

The fundamental idea of the invention consists in configuring the illumination system in such a way that the imaging region of the inner surface captured by the optical system is illuminated partially under brightfield illumination and partially under darkfield illumination. In brightfield illumination, in which the light reflected by the inner surface to be imaged is used for imaging, an especially high contrast image is produced with which it is possible to detect, for example and in particular, scratches and porosities in the inner surface to be imaged. Conversely, other structural defects, such as, for example, casting defects in cast-iron parts, can be detected with a darkfield illumination in which the beam path of the light is routed so as to utilize primarily those rays scattered from the inner surface to be imaged for the purpose of imaging.

The apparatus according to the invention thus enables the inner surface for imaging to be imaged both under brightfield illumination and also darkfield illumination. The apparatus according to the invention thus combines the advantages that exist for both illumination methods in terms of detecting defects. According to the invention, it is possible here to image a first axial section of the imaging region under brightfield illumination and simultaneously image a second axial section of the imaging region, which section is at a distance from the first axial section, under darkfield illumination, with the result that both brightfield illumination and darkfield illumination are performed simultaneously. However, it is also possible according to the invention to image one and the same axial section of the inner surface to be imaged in chronological succession both under darkfield illumination as well as brightfield illumination. For example, a feed device can be associated with the apparatus, by which device the apparatus is axially movable relative to the inner surface to be imaged. If, for example, an examined section of the inner surface examined under darkfield illumination is located in the feed direction obliquely in front of the optical system, while a section examined under brightfield illumination is located in the axial direction of the cavity approximately at the level of the optical system, or somewhat behind this system, a predetermined axial region of the inner surface can be imaged during the feed motion first under darkfield illumination, and then imaged during a continued feed motion of the apparatus under brightfield illumination.

In this way, the possible capabilities of the apparatus according to the invention are expanded in terms of imaging the inner surface of the cavity.

As a result, that fact that imaging can be effected according to the invention both under brightfield illumination and darkfield illumination means that test procedures are made possible by the device according to the invention that are especially comprehensive and highly informative in terms of detecting surface defects.

The device according to the invention is of relatively simple construction, and thus relatively inexpensive to produce.

According to the invention, it is in principle possible to provide an illumination system comprising two or more light sources, of which one light source is provided to effect the brightfield illumination in the first axial section of the imaging region and a second light source is provided to effect the darkfield illumination in the second axial section. In order to create an especially simple construction of the apparatus according to the invention, an advantageous embodiment of the invention provides a mirror arrangement or system, the reflection surfaces or reflective surfaces of which are disposed partially within the beam path of the light source such that, when the apparatus is in the imaging position, partial beams of the light emitted by the light source strike the second axial section of the imaging region and the reflective surface reflects other partial beams onto the first axial section. In this embodiment, the simultaneous brightfield illumination and darkfield illumination, provided according to the invention, of different axial sections on the inner surface of the cavity are thus able to be realized by means of a single light source. Those partial beams of the emitted light that are reflected from the reflective surface onto the first axial section can function, for example, to effect the brightfield illumination, while those partial beams that pass through the reflective surface of the mirror arrangement onto the second axial section can function to effect the darkfield illumination.

In an advantageous development of the above-mentioned embodiment, provision is made whereby the mirror arrangement has an annular reflective surface. This then achieves an annular illumination of the inner surface of the workpiece. Depending on the specific requirements, the reflective surface of the mirror arrangement can be on average configured as straight, with the result that the mirror is of a frustoconical shape. However, the reflective surface can also have a cross section embodied as a circular, aspheric, or parabolic cross section, or a cross section embodied in some other way.

In another embodiment of the invention, provision is made whereby, the reflective surface is coaxial relative to the optical axis of the optical system. In this manner an illumination that is uniform in the circumferential direction of the inner surface is achieved.

In particular when the illumination system emits in the direction of the optical axis of the optical system, it is advantageous for the reflective surface to be disposed at an angle at least in certain sections, as is provided by another advantageous development of the embodiment comprising the mirror arrangement.

In an extraordinarily advantageous embodiment of the invention, provision is made whereby the optical system includes an image angle of >180°, preferably of about 185°. In this embodiment, by way of example and in particular simultaneously, one section can be imaged that is disposed obliquely in the direction of the optical axis in front of the optical system and is illuminated under darkfield illumination, while one section of the inner surface can be imaged that is disposed in the direction of the optical axis at the level of the optical system or right behind the optical system, and is illuminated under brightfield illumination.

In order to achieve a uniform illumination of the sections or of the sections of the inner surface to be illuminated, an advantageous embodiment of the invention provides that the illumination system have an annular light source. By way of example and in particular, the annular light source can be composed of an arrangement of multiple light-emitting diodes that are disposed behind a diffuser.

In order to achieve an especially compact and space-saving configuration for the apparatus, it is advantageous to dispose the light source in alignment with the optical axis within the immediate proximity of the optical system.

In another advantageous embodiment of the invention, the light source is disposed coaxially relative to the optical axis of the optical system.

Another advantageous embodiment provides that the light source emit essentially coaxially relative to the optical axis of the optical system.

The imager of the apparatus according to the invention, can be of any appropriate construction. For example, it is possible for the imager to use an annular sensor that captures an annular region of the image circle. However, an advantageous embodiment of the invention provides an approach whereby the imager is constructed to capture the entire image circle of the optical system. In this embodiment, the capture of the entire image circle by the optical system in particular provides the capability of simultaneously imaging multiple annular regions on the inner surface of the workpiece, of which regions at least one can be illuminated under brightfield illumination and at least one can be illuminated under darkfield illumination.

In order to allow for complete imaging of the inner surface in the axial direction of the cavity, it is advantageous to provide a feed device that provides an axial feed of the apparatus relative to the workpiece.

Storage of the image data recorded by the imager, which can preferably have a digital image sensor, can be implemented by any appropriate approach. In this regard, an advantageous embodiment provides a storage device to store the image data according to the given axial position of the apparatus relative to the workpiece. In this embodiment, different annular regions of the inner surface of the cavity are imaged in chronological succession during an axial feed motion by the apparatus and the image data thus obtained is stored, wherein a correlation is created between the given axial position of the apparatus and the given stored image data.

In order to provide complete imaging circumferentially, it is advantageous for the optical system to include a panoramic field of view of 360°. Appropriate optical systems of this type are disclosed, for example, in U.S. Pat. No. 3,552,820, U.S. Pat. No. 5,473,474, U.S. Pat. No. 4,565,763 and EP 1 321 793 B1.

The apparatus according to the invention is suitable for inspecting any inner surfaces of a cavity, in particular, rotationally-symmetrical, for example, cylindrical or essentially cylindrical cavities. In an advantageous embodiment of the invention, provision is made whereby the inner surface to be imaged is of substantially rotationally-symmetrical shape, in particular, is formed by a cylinder bore of a crankcase.

The following discussion describes the invention in more detail based on the attached drawing in which highly-schematic exemplary embodiments of an apparatus according to the invention are illustrated. Here all described features illustrated in the drawing and claimed in the claims are the subject matter of the invention, both taken alone and in any combination with each other, irrespective of their combination in the claims and the references of the claims, as well as irrespective of their description or illustration in the drawing.

BRIEF DESCRIPTION OF THE DRAWINGS

FIG. 4 is the same view as in FIG. 1 showing a second embodiment of an apparatus according to the;

DETAILED DESCRIPTION OF THE INVENTION

In the figures, identical or corresponding components are provided with identical reference numerals.

Figure 1:
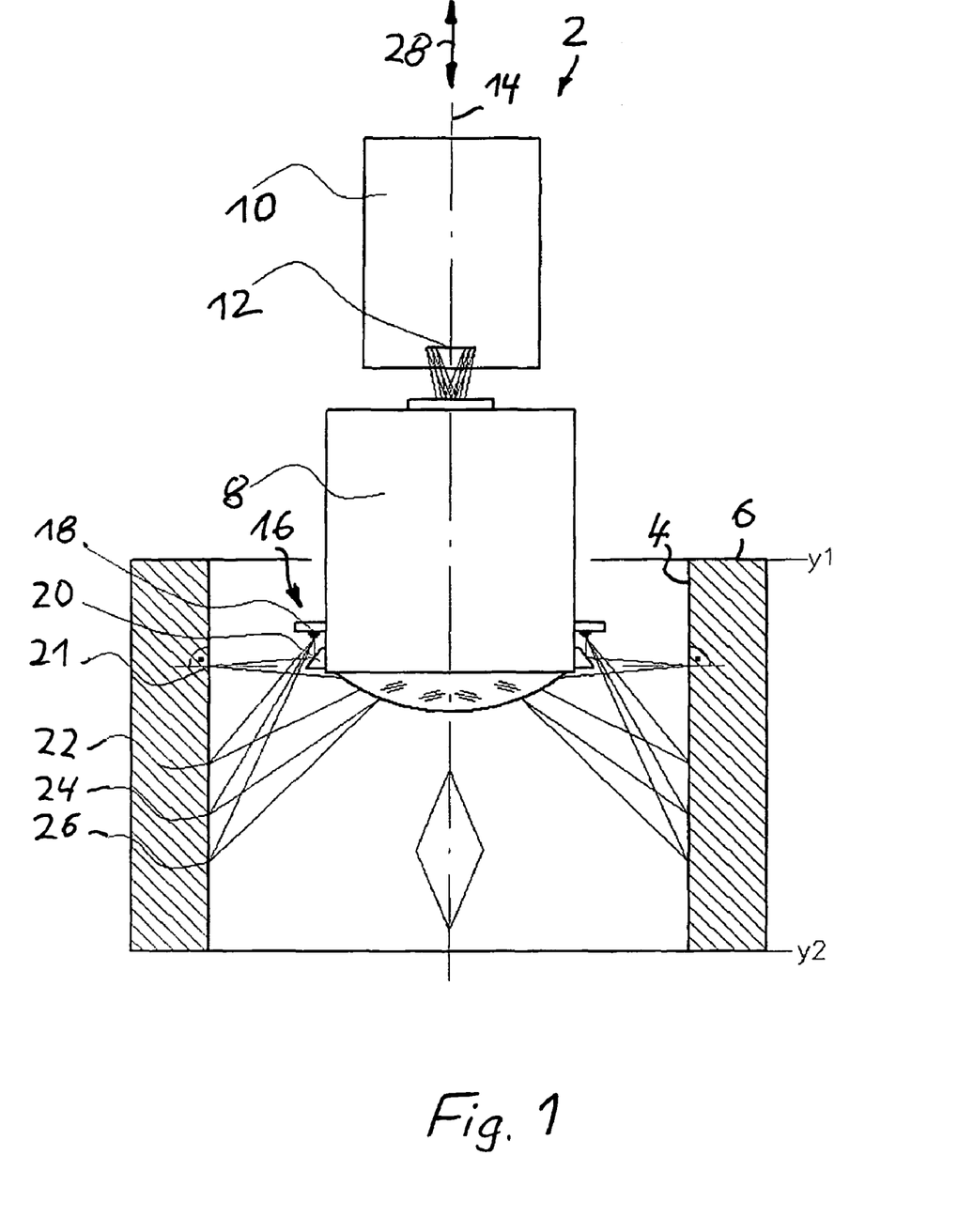
FIG. 1 is a schematic side view of a first exemplary embodiment of an apparatus according to the invention in the imaging position.

FIG. 1 illustrates a first embodiment of an apparatus 2 according to the invention for imaging of an inner surface 4 of a cavity of a workpiece 6. Inner surface 4 in the embodiment illustrated involves an inner surface of a cylinder bore of a crankcase. Apparatus 2 has an optical system 8 having a panoramic field of view in this embodiment of 360° that is linked to an image capturing device (imager) 10 and a following evaluation device by an image communication link, not shown. In this embodiment, imager 10 is composed of a digital camera having an image sensor 12. Optical system 8 in the embodiment illustrated in FIG. 1 includes a refraction-optical-imaging fisheye objective lens, the optical axis of which in FIG. 1 is identified by a dot-dash line 14

In the embodiment illustrated, optical system 8 has an angular field of >180°, specifically, approximately 185°, such that optical system 8 captures not only a region of inner surface 4 that is situated obliquely in front of the front lens but also a region of inner surface 4 lying further back relative to the front lens of optical system 8.

In the illustrated embodiment, imager 12 is configured to capture the entire image circle of optical system 8. Images captured by optical system 8 are recorded by image sensor 12 of imager 10 and stored in a storage device, not shown.

Apparatus 2 includes an illumination system 16, which according to the invention is disposed in such a way relative to optical system 8, and for which the beam path is selected in such a way, that a first axial section of the imaging region is able to be illuminated under brightfield illumination, while simultaneously a second axial region at a distance from the first axial region is able to be illuminated under darkfield illumination. In the illustrated embodiment, illumination system 16 has an annular light source 18 that in this embodiment is composed of a plurality of light-emitting diodes disposed along a circular ring, the diodes irradiating an annular diffuser. As seen in FIG. 1, light source 18 is disposed in the immediate proximity of optical system 8 in the axial direction of the optical axis. As is also seen in FIG. 1, light source 18 is oriented coaxially relative to optical axis 14 and emits essentially coaxially relative to optical axis 14 of optical system 8.

In the embodiment illustrated, illumination system 16 has a mirror arrangement or mirror system 20 that in this embodiment is composed of a toroidal mirror, the reflection surface or reflective surface 20 of which is inclined relative to optical axis 14 of optical system 8. In the embodiment illustrated, reflective surface 20 has an aspheric cross-section. As is seen in FIG. 1, reflection surface 20 is disposed partially within the beam path from light source 18 in such a way that in the imaging position of apparatus 2 shown in FIG. 1 reflective surface 20 reflects partial beams of the light emitted by light source 18 on a first axial section along inner surface 4. A corresponding partial beam is identified in FIG. 1 by reference number 21. Other partial beams pass by reflective surface 20 to directly strike inner surface 4. In FIG. 1, the corresponding partial beams are identified, by way of example, by reference numbers 22, 24, 26. As is seen in FIG. 1, the first axial section of the imaging region in which partial beam 21 strikes inner surface 4 is at a certain distance in the axial direction of optical axis 14 from the second axial section in which partial beams 22, 24, 26 strike inner surface 4. Both the first axial section and the second axial section are located within the imaging region of optical system 8.

As is seen in FIG. 1, although the first axial section is located somewhat behind optical system 8 in the direction of the optical axis it is nevertheless captured by the imaging region due to the image angle of 185° for optical system 8.

In the embodiment illustrated, a brightfield illumination is effected by the partial beams of the light emitted by light source 18 that are reflected from reflective surface 20 onto inner surface 4, while the darkfield illumination is effected by partial beams 22, 24, 26. As a result, according to the invention a first axial section of the imaging region—the first axial section associated with partial beam 21 in the embodiment illustrated—is able to be illuminated under brightfield illumination, while simultaneously a second axial section at a distance from the first axial section—the section associated with partial beams 22, 24, 26 in the embodiment—is able to be illuminated under darkfield illumination. Thus, the first axial section (under brightfield illumination) and the second axial section (under darkfield illumination) are able to be imaged simultaneously or in chronological succession by means of apparatus 2 according to the invention.

The functional principle of apparatus 2 according to the invention is as follows:

In order to image inner surface 4 of the cavity in workpiece 6, apparatus 2 is movable by means of a feed device (not shown) in the direction of the double-headed arrow 28 relative to workpiece 6.

The first axial section is illuminated under brightfield illumination (partial beam 21) and the second axial section (partial beams 22, 24, 26) of inner surface 4 is illuminated under darkfield illumination by means of illumination system 16, and these are imaged by means of optical system 8 on image sensor 12.

Figure 2:
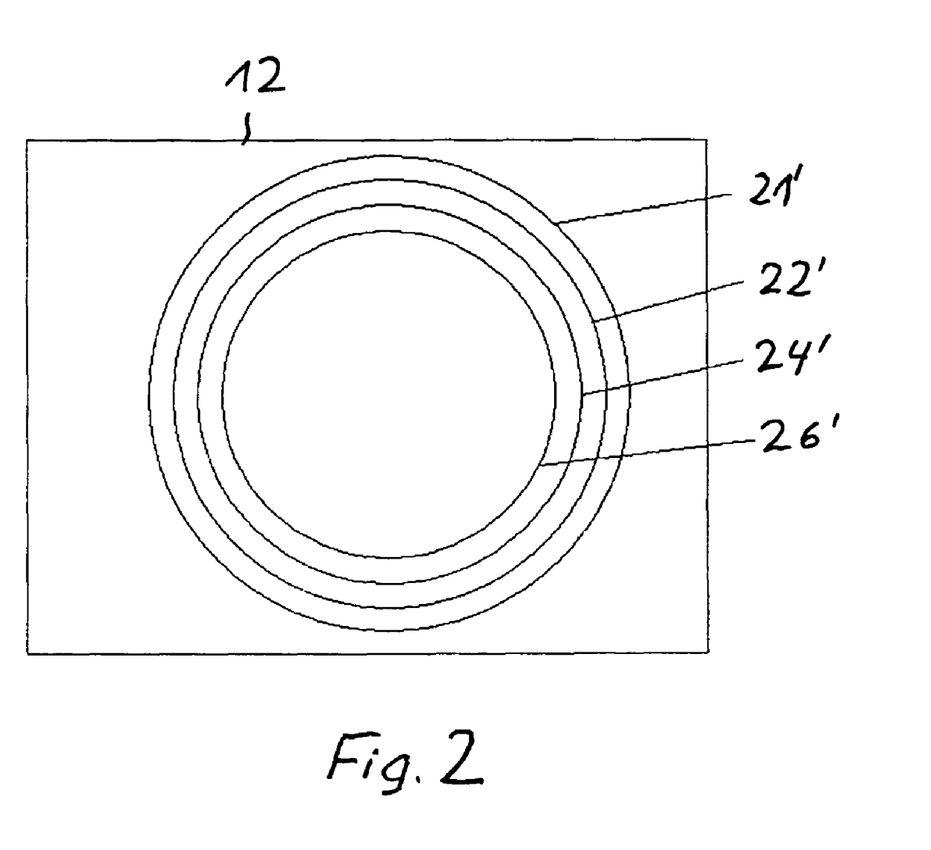
FIG. 2 is an image on an imager of the apparatus of FIG. 1.

Since image sensor 12 is configured to capture the entire image circle of optical system 8, multiple annular regions on inner surface 4 can be imaged simultaneously, as is illustrated in FIG. 2. FIG. 2 illustrates by reference numbers 21', 22', 24', and 26' which of the annular regions imaged by image sensor 12 correspond to respective partial beams 21, 22, 24, and 26.

During the feed of apparatus 2 relative to workpiece 6, successively different axial regions of inner surface 4 are imaged and converted in the evaluation unit to images, each of which corresponds to a developed view of inner surface 4.

Figure 3:
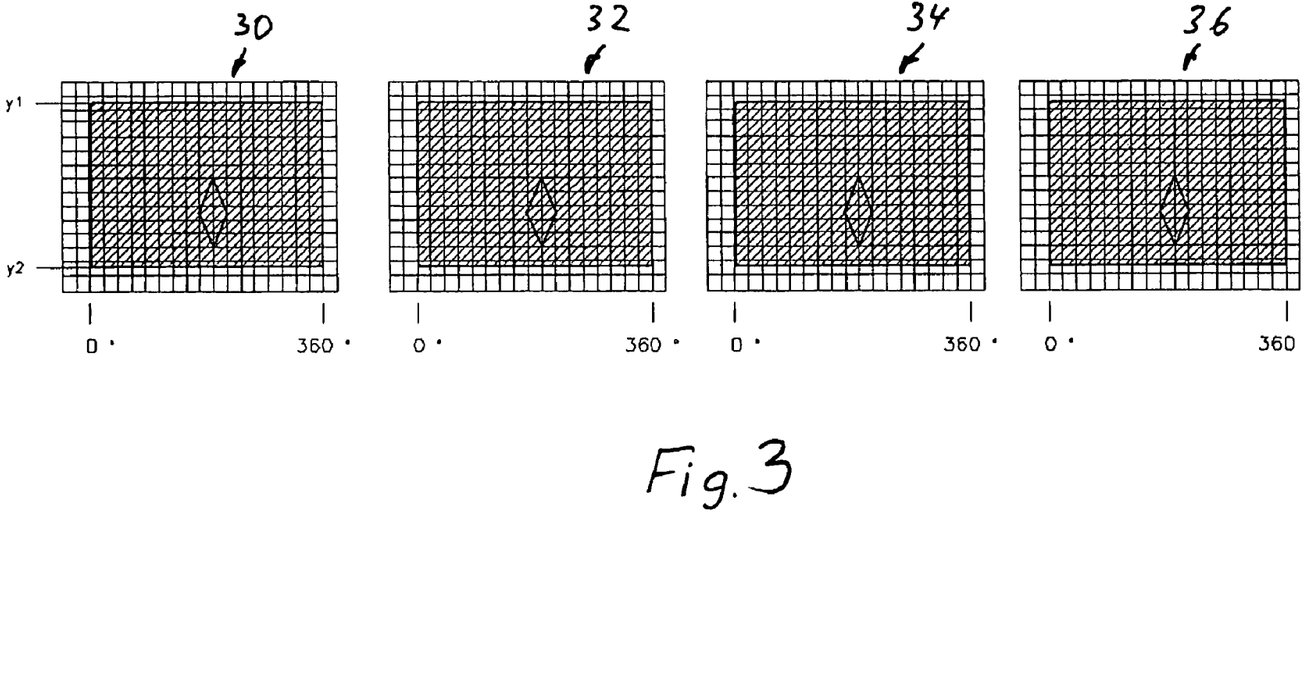
FIG. 3 is digital images generated as in FIG. 1 of developed views of the inner surface to be imaged in the bright field and dark field.

FIG. 3 illustrates the corresponding images 30, 32, 34, 36 in an image storage means of the evaluation unit, where image 30 corresponds to an imaging under brightfield illumination and images 32, 34, 36 corresponding to an imaging under darkfield illumination. The means by which the evaluation unit converts the circular regions (see FIG. 2) to a Cartesian image is known, for example, from DE 10 2007 031 358 A1, the disclosure of which is herewith incorporated by reference in the present application.

Based on the images recorded under brightfield illumination or darkfield illumination, it is possible to determine whether inner surface 4 to be inspected meets predetermined requirements in terms of its surface quality.

Surface defects are able to be detected especially reliably due to the fact that the inner surface can be imaged both under brightfield illumination and also under darkfield illumination.

Figure 4:
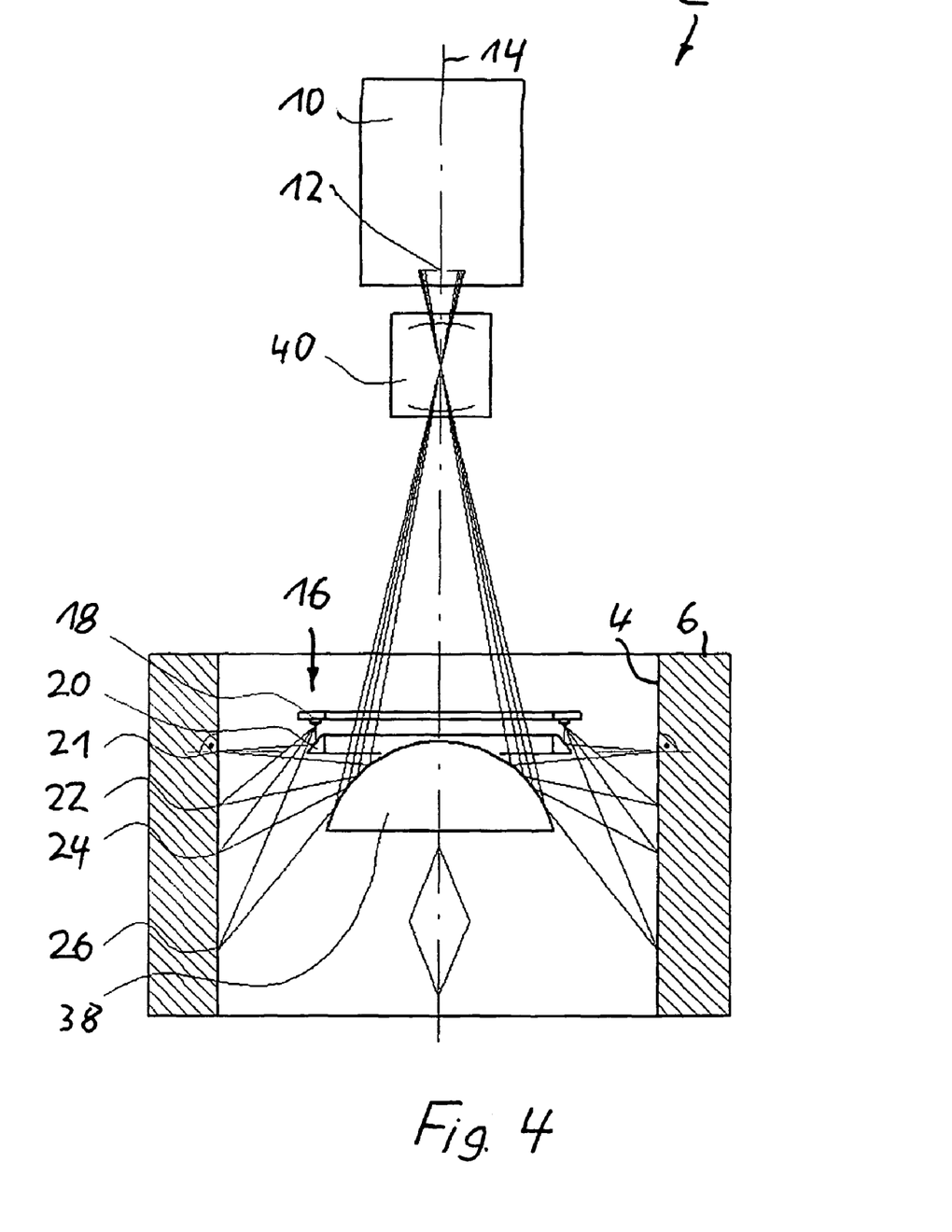

FIG. 4 illustrates a second embodiment of apparatus 2 according to the invention that differs from the embodiment of FIG. 1 in that instead of a purely refraction-optically imaging optical system a catadioptric optical system is provided that in this embodiment comprises an imaging mirror 38 and an imaging objective lens 40. In FIG. 4, imaging mirror 38 is illustrated, simply by way of example, as a spherical segment. However, it can also be configured as conoidal or having any other desired cross-section—for example, an aspheric or convex cross-section—depending on specific requirements.

Figure 5:
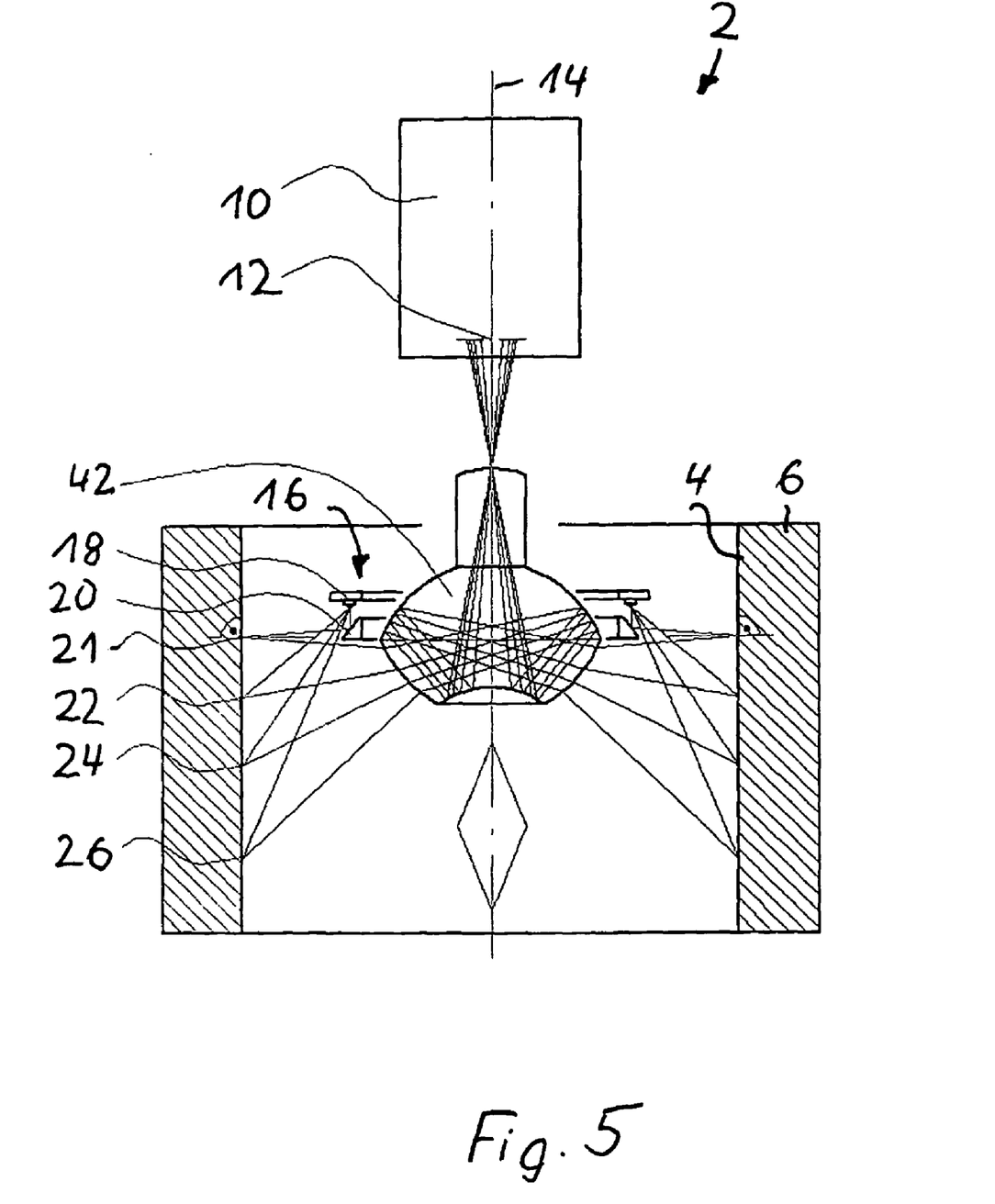
FIG. 5 is the same view as in FIG. 1 showing a third embodiment of an apparatus according to the invention.

FIG. 5 illustrates a third embodiment of apparatus 2 according to the invention in which a catadioptric optical system 42 is used, matching the embodiment of FIG. 4. In order to improve the imaging quality, optical catadioptric optical system 42 has the configuration disclosed in U.S. Pat. No. 4,566,763.

Figure 6:
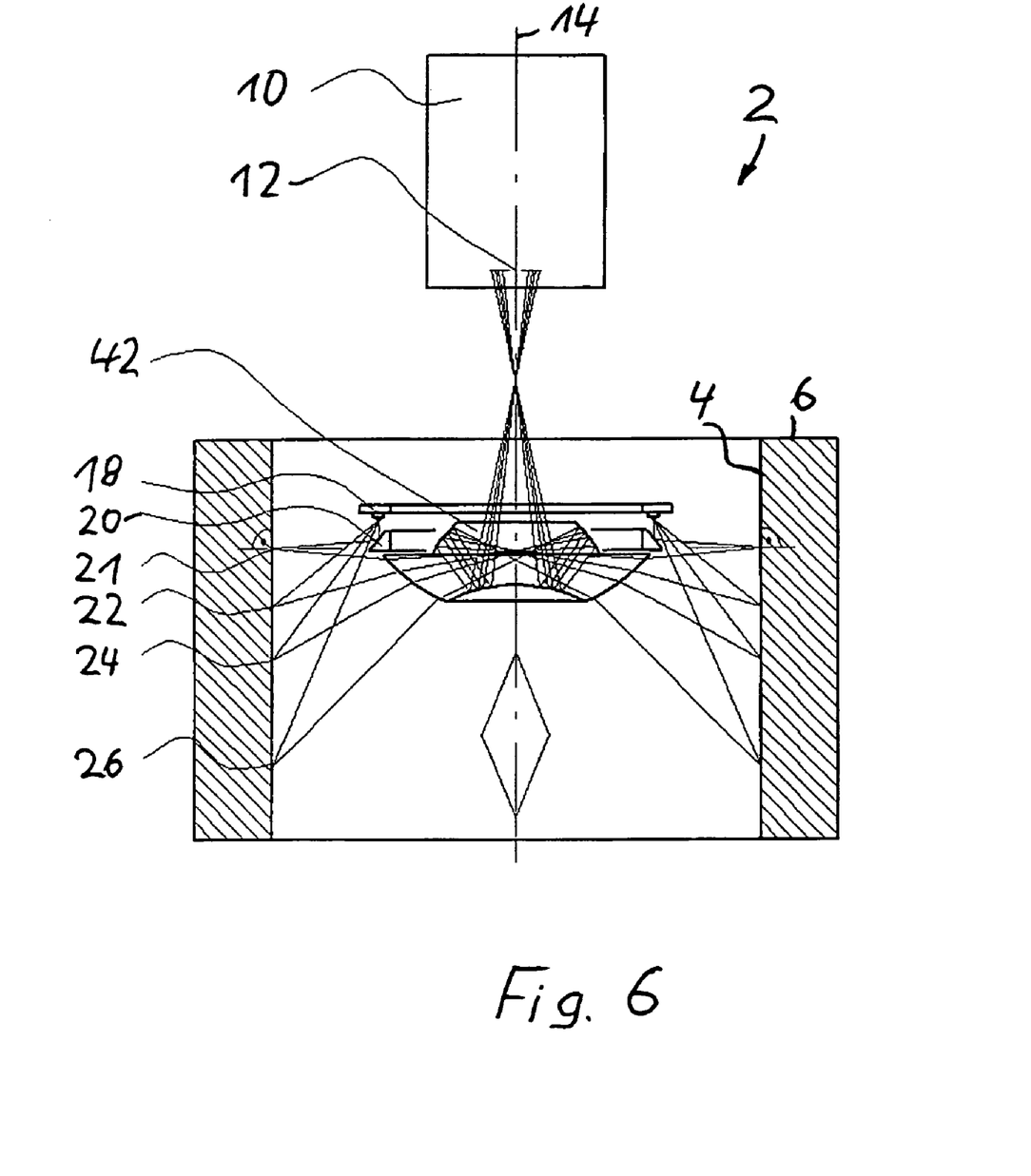
FIG. 6 is the same view as in FIG. 1 showing a fourth embodiment of an apparatus according to the invention.

FIG. 6 illustrates a fourth embodiment of apparatus 2 according to the invention, in which catadioptric optical system 42 has the configuration of disclosed in U.S. Pat. No. 5,473,474.

Figure 7:
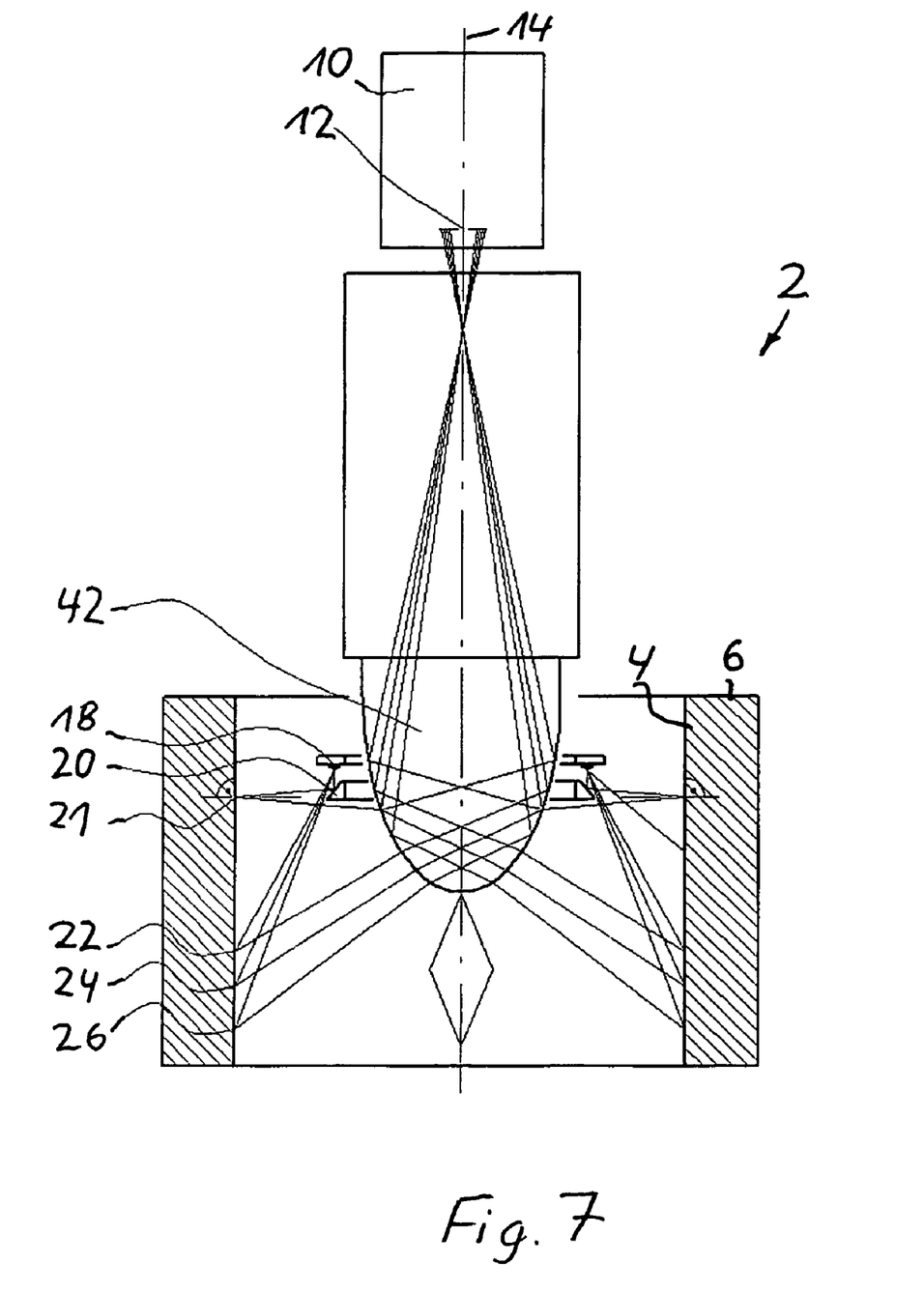
FIG. 7 is the same view as in FIG. 1 showing a fifth embodiment of an apparatus according to the invention.

FIG. 7 illustrates a fifth embodiment of apparatus 2 according to the invention in which catadioptric optical system 42 has the configuration disclosed in U.S. Pat. No. 3,552,820.

Figure 8:
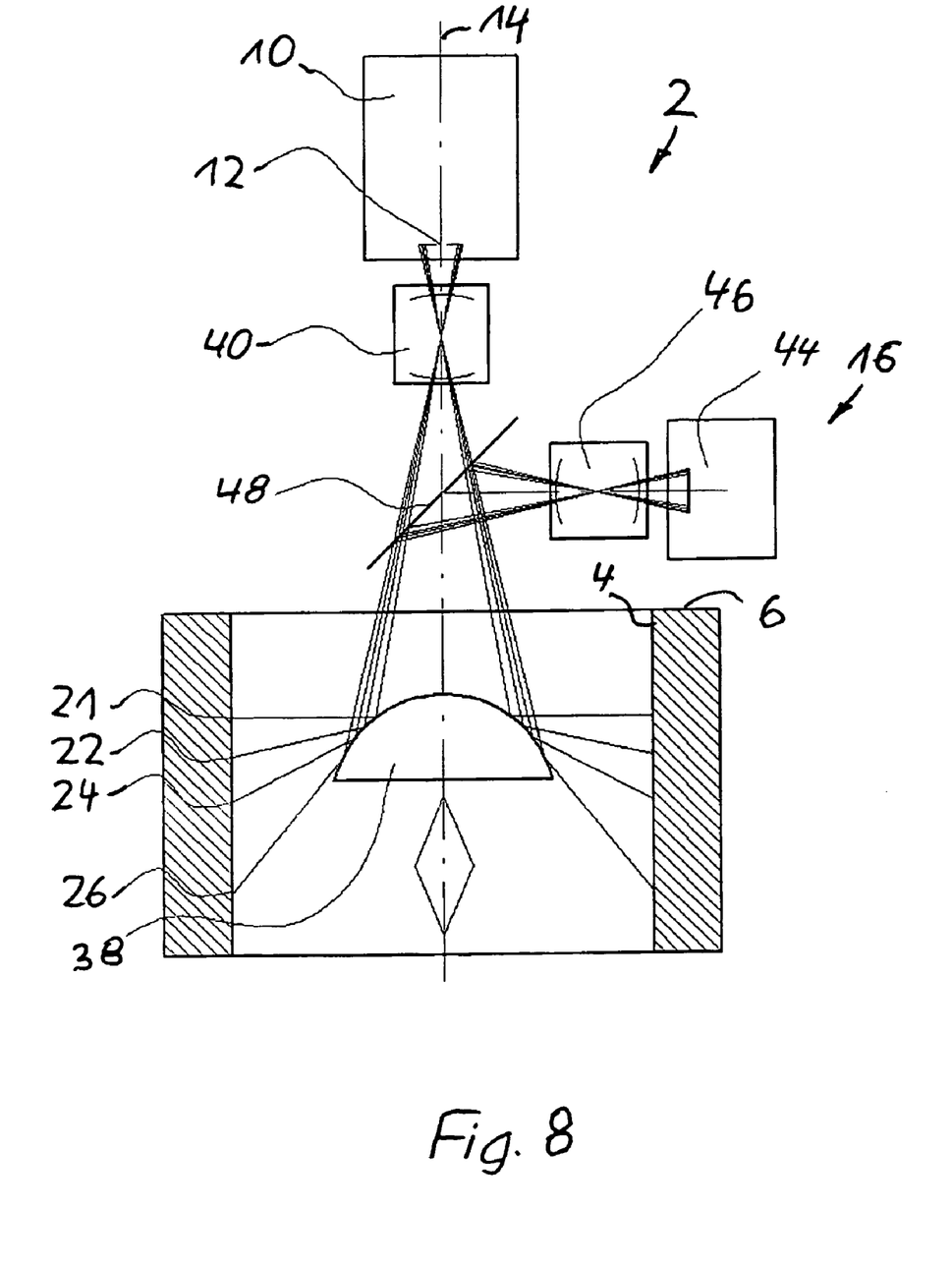
FIG. 8 is the same view as in FIG. 1 showing a sixth embodiment of an apparatus according to the invention.

FIG. 8 illustrates a sixth apparatus 2 according to the invention that differs from the embodiment of FIG. 4 in terms of illumination system 16. Illumination system 16 has in this embodiment a light source 44 that can be implemented, for example, as an LED light bulb, short-arc lamp, or the like. An illumination condenser is disposed in the beam direction in front of light source 44 to project light source 44, where the light path of the light generated by light source 44 is congruent to the imaging beam path. The light emitted by the light source is directed by semi-transparent deflection mirror 48 onto imaging mirror 38.

Figure 9:
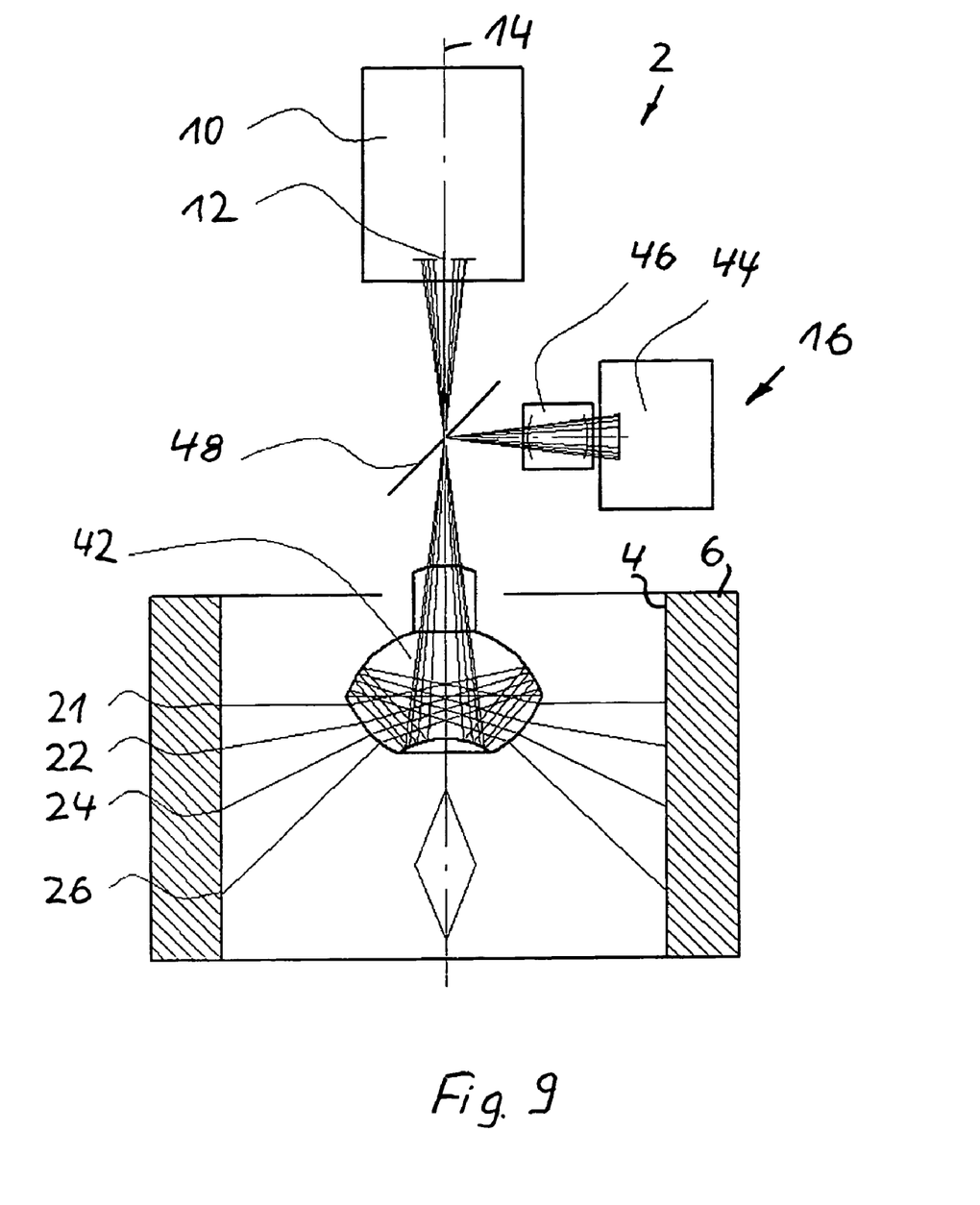
FIG. 9 is the same view as in FIG. 1 showing a seventh embodiment of an apparatus according to the invention.

FIG. 9 shows a seventh embodiment of an apparatus according to the invention that differs from the embodiment of FIG. 8 in that a catadioptric optical system 42 used is in accordance with FIG. 5.

Figure 10:
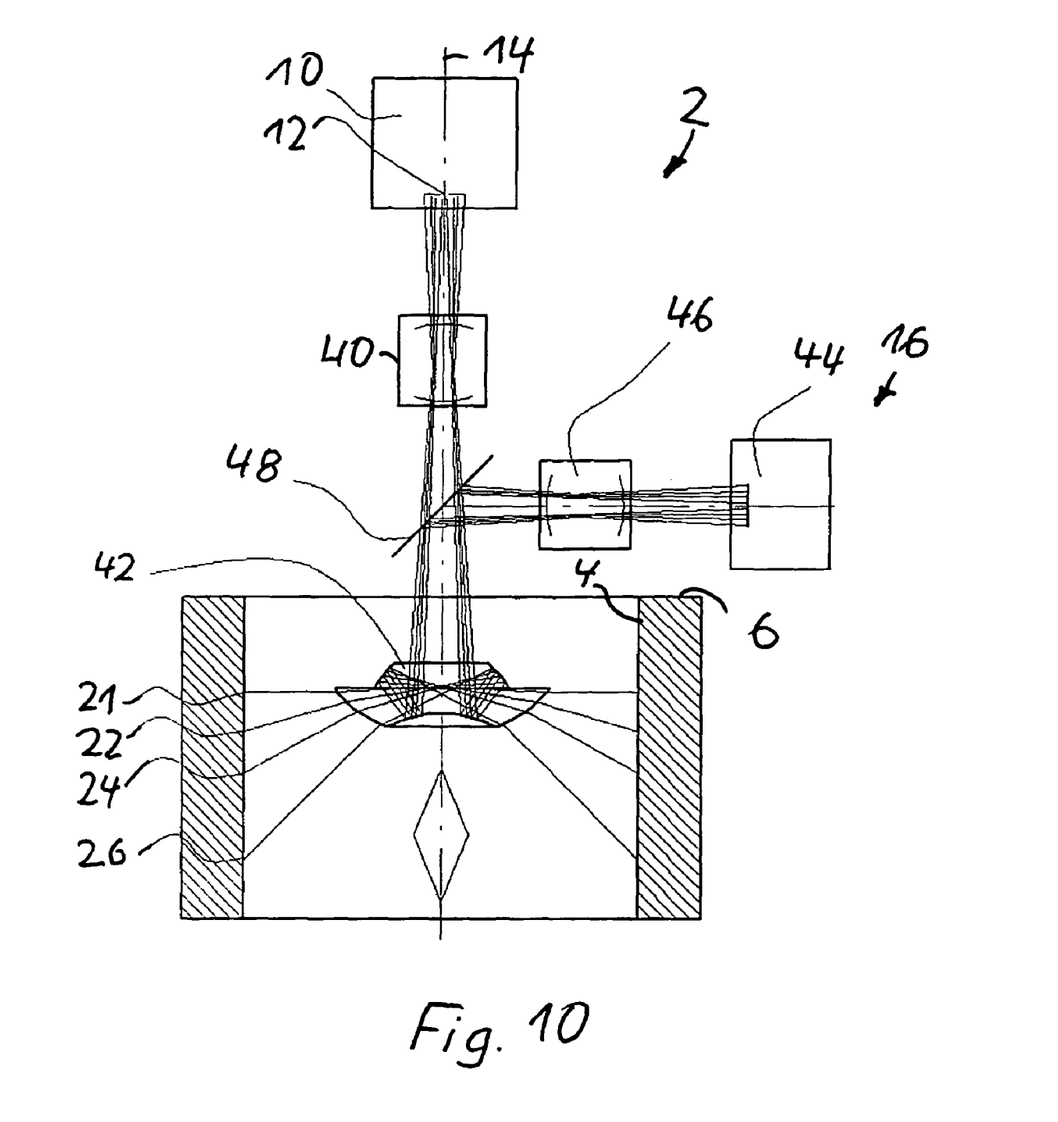
FIG. 10 is the same view as in FIG. 1 showing an eighth embodiment of an apparatus according to the invention.

FIG. 10 illustrates an eighth embodiment of apparatus 2 according to the invention that differs from the embodiment of FIG. 8 in that catadioptric optical system 42 used is in accordance with FIG. 6.

Figure 11:
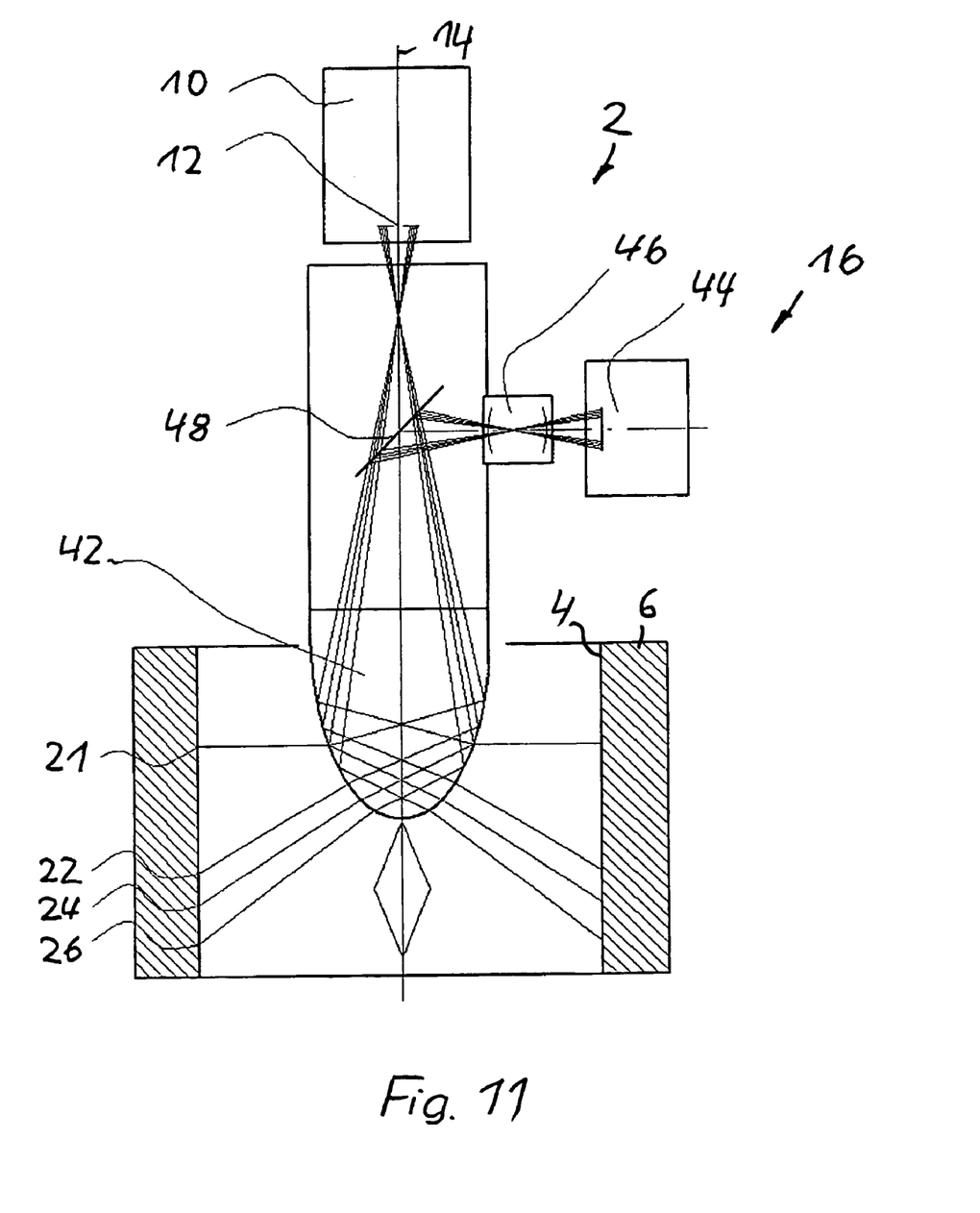
FIG. 11 is the same view as in FIG. 1 showing a ninth embodiment of an apparatus according to the invention.

FIG. 11 illustrates a ninth embodiment of apparatus 2 according to the invention that differs from the embodiment of FIG. 8 in that catadioptric optical system 42 used is in accordance with FIG. 7. While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. Apparatus for imaging an inner surface of a cavity in a workpiece, comprising:
   a) an optical system having a panoramic field of view that is linked to an imager and a downstream evaluation device with an image communication link;
   b) an illumination system having a light source to illuminate an imaging region of the inner surface captured by the optical system; and
   c) the illumination system is disposed relative to the optical system, and a beam path of the light source is selected, so that a first axial section of the imaging region is able to be illuminated under brightfield illumination, while simultaneously a second axial region axially spaced apart from the first axial region is able to be illuminated under darkfield illumination.

2. Apparatus according to claim 1, wherein:
   a) a mirror system is provided, and the reflection surface of the mirror system is disposed partially within the beam path of the light source such that in an imaging position of the apparatus partial beams of the light emitted by the light source strike the second axial section of the imaging region and the reflection surface reflects other partial beams onto the first axial section.

3. Apparatus according to claim 2, wherein:
   a) the mirror system includes an annular reflection surface.

4. Apparatus according to claim 2, wherein:
   a) the reflection surface is coaxial relative to the optical axis of the optical system.

5. Apparatus according to claim 2, wherein:
   a) the reflection surface is disposed at least sectionally at an angle relative to the optical axis of the optical system.

6. Apparatus according to claim 1, wherein:
   a) the optical system includes an angular field of >180°.

7. Apparatus according to claim 1, wherein:
   a) the illumination system includes an annular light source.

8. Apparatus according to claim 7, wherein:
   a) the light source is disposed in the axial direction of the optical axis directly adjacent the optical system.

9. Apparatus according to claim 7, wherein:
   a) the light source is disposed coaxially relative to the optical axis of the optical system.

10. Apparatus according to claim 7, wherein:
    a) the light source emits substantially coaxially relative to the optical axis of the optical system.

11. Apparatus according to claim 1, wherein:
    a) the imager is configured to capture the entire image circle of the optical system.

12. Apparatus according to claim 1, wherein:
    a) a feed device for axially feeding the apparatus relative to the workpiece is provided.

13. Apparatus according to claim 1, wherein:
    a) a storage device to store the image data according to the given axial position of the apparatus relative to workpiece is provided.

14. Apparatus according to claim 1, wherein:
    a) the optical system has a 360° panoramic field of view is provided.

15. Apparatus according to claim 1, wherein:
    a) the inner surface to be imaged is of essentially rotationally-symmetrical shape.

16. Apparatus according to claim 15, wherein:
    a) the essentially rotationally-symmetrical shape to be imaged is formed by a cylinder bore of a crankcase.

17. Apparatus according to claim 1, wherein:
    a) the optical system includes an angular field of about 185°.

\* \* \* \* \*